United States Patent [19]

Hieb et al.

[11] Patent Number: 5,232,667

[45] Date of Patent: Aug. 3, 1993

[54] TEMPERATURE CONTROL FOR PORTABLE DIAGNOSTIC SYSTEM USING A NON-CONTACT TEMPERATURE PROBE

[75] Inventors: Martin G. Hieb, Roseville; Scott E. Blomberg, St. Anthony Village, both of Minn.

[73] Assignee: Diametrics Medical, Inc., Roseville, Minn.

[21] Appl. No.: 886,616

[22] Filed: May 21, 1992

[51] Int. Cl.⁵ .................. G01N 27/28; G05D 23/27
[52] U.S. Cl. ......................... 422/82.04; 204/408; 204/412; 204/416; 374/121; 374/141; 422/68.1; 422/82.01; 422/82.02; 422/82.03; 422/99; 422/105; 422/109
[58] Field of Search ............. 422/68.1, 82.01, 82.02, 422/82.03, 82.04, 99, 105, 109, 98; 204/153.1, 408, 412, 416; 374/121, 141

[56] References Cited

U.S. PATENT DOCUMENTS

| | | | |
|---|---|---|---|
| 4,225,410 | 9/1980 | Pace | 204/412 |
| 4,271,119 | 6/1981 | Columbus | 204/416 X |
| 4,361,540 | 11/1982 | Weinberg et al. | 422/82.04 X |
| 4,397,725 | 8/1983 | Enzer et al. | 422/98 X |
| 4,453,151 | 6/1984 | Leary et al. | 422/98 X |
| 4,654,127 | 3/1987 | Baker et al. | 422/82.04 X |
| 4,654,624 | 3/1987 | Hagan et al. | 422/98 X |
| 4,762,594 | 8/1988 | Guruswamy | 204/416 X |
| 4,786,394 | 11/1988 | Enzer et al. | 204/412 X |
| 4,831,258 | 5/1989 | Paulk et al. | 374/121 X |
| 4,929,426 | 5/1990 | Bodai et al. | 422/82.04 X |
| 4,988,211 | 1/1991 | Barnes et al. | 374/121 |

FOREIGN PATENT DOCUMENTS 8800708 1/1988 PCT Int'l Appl. ............... 422/82.03

*Primary Examiner*—James C. Housel
*Assistant Examiner*—Arlen Sodenquist
*Attorney, Agent, or Firm*—Haugen and Nikolai

[57] ABSTRACT

An accurate, low cost temperature control system for a disposable cartridge carrying including a sample chamber for a portable medical diagnostic device or other electrochemical analytical device is disclosed. The disposable cartridge may include its own heating element on a sensor chip and plugs into a terminal which contains electrical input/output connections. The outer surface of the chip is exposed. A remote temperature sensor which senses the temperature of the outer surface of the chip of the measuring cell and generates a control signal which is used with conventional temperature control circuitry as the basis for thermostatic control of the cell temperature.

11 Claims, 4 Drawing Sheets

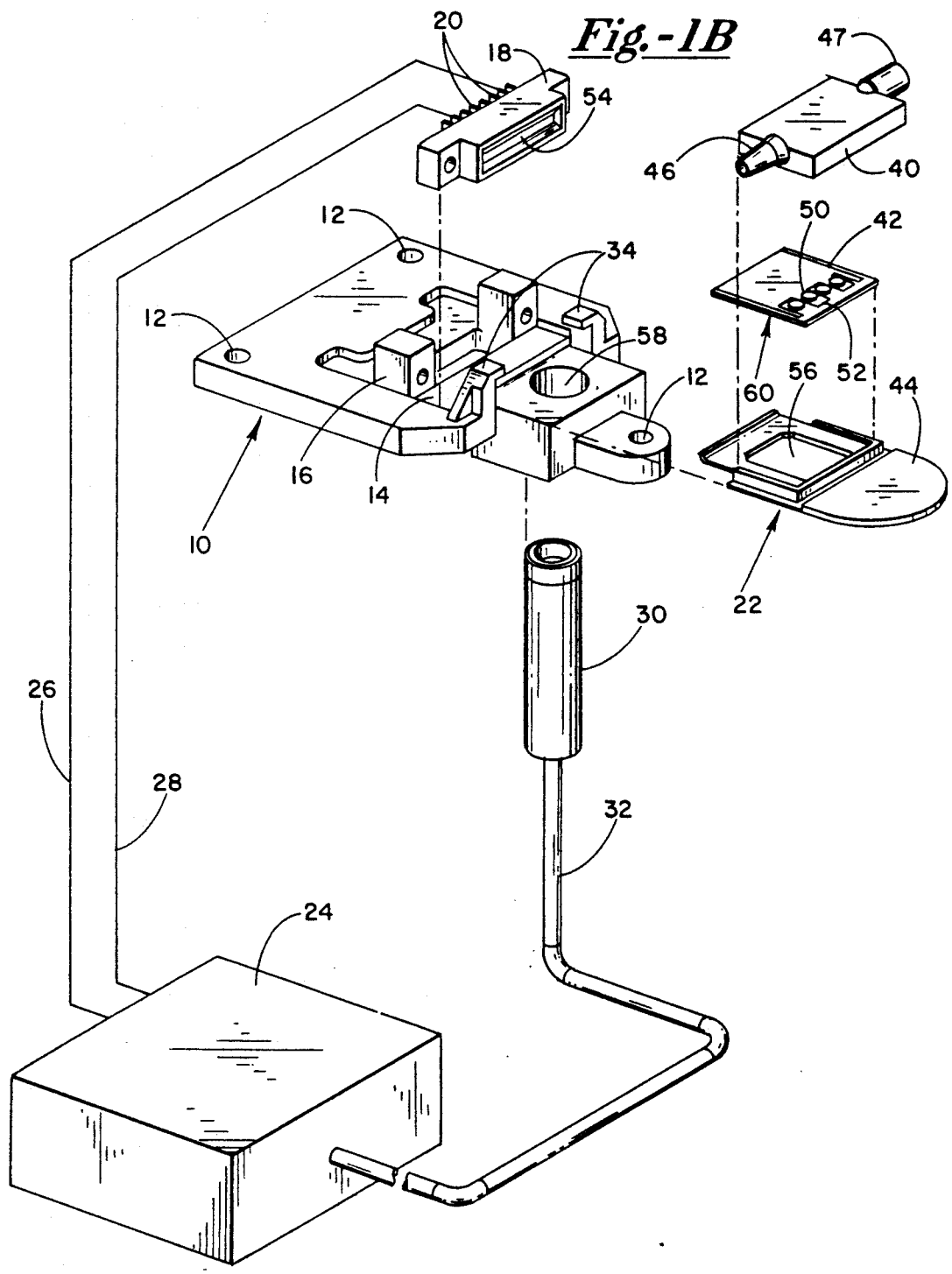

ic cell of a cartridge in accordance with the invention including reaction to induced traumatic temperature stimuli.

TEMPERATURE CONTROL FOR PORTABLE DIAGNOSTIC SYSTEM USING A NON-CONTACT TEMPERATURE PROBE

BACKGROUND OF THE INVENTION

I. Field of the Invention

The present invention is directed generally to portable diagnostic systems based on electrochemical determinations in biological samples in which the control of sample temperature is important to analytical accuracy. More particularly, the invention concerns a system for controlling the temperature in a removable disposable cartridge sampling unit for use with a portable diagnostic system. The system achieves rapid heating to and accurate control at a predetermined set point without the need for contact between any temperature measuring device and the disposable cartridge unit itself.

II. Related Art

Methods and devices utilized for determining concentrations of electroactive species in solution using electrochemical or electrolytic methods such as, for example, the determination of $pO_2$, $pCO_2$ and electrolytes in blood samples, are well known. These instruments typically include a pair of electrochemical half cells, one of which is used as the sensor or sample half cell and the other as a reference electrode or a reference half cell. As is the case with any concentration determination of dissolved gaseous species in a liquid, the temperature at which the electrochemical determination is made needs to be known. Traditionally, blood gas determinations, for example, have been made utilizing permanently installed laboratory instrumentation to which samples are brought for analysis. Of course, in such instruments the temperature at which the sample is analyzed can be readily controlled as by a constant temperature oven, or the like. This, of course, is not practical in the case of a small portable device.

Thus, there remains a need for an inexpensive approach to controlling the sample temperature in a portable blood gas analyzer or other such instrument that is easily manufactured and rapidly stabilizing and accurate. Accordingly, it is a primary object of the present invention to provide a temperature control system for use in conjunction with a portable analytical device which is simple, reacts rapidly and accurately controls sample temperature.

It is a further object of the present invention to provide a non-contact temperature measurement system for a disposable test cartridge, so that prolonged or repeated use will not physically wear components to a state of unreliability.

Yet another object of the present invention is to provide a temperature control system for a disposable cartridge electrochemical cell sampling device in which the disposable cartridge carries its own inexpensive internal resistive heating element to heat the sample environment. A still further object of the invention is to provide a temperature control system for such a disposable cartridge which uses a temperature sensor that need not be directly connected to the disposable cartridge.

These and other objects will become apparent to those skilled in the art in accordance with the descriptions and drawings herein.

SUMMARY OF THE INVENTION

The present invention provides an accurate, low cost temperature control system for a portable medical diagnostic device or other portable electrochemical analytical device which requires measurements to be made at a controlled temperature. In the preferred embodiment, a disposable cartridge carries an electrochemical sensing cell including the sample chamber. The disposable cartridge includes its own resistive heating element on a sensor chip and plugs into a terminal connector which contains the necessary electrical input/output connections. The opposite or outer surface of the chip is at least partially exposed to ambient air. A separate sensor probe is provided which senses the temperature of the outer surface of the chip of the measuring cell and uses that sensed temperature to generate a signal which is used in conjunction with conventional temperature control circuitry which is designed with a control set point and which thermostatically controls the resistive heater element to rapidly reach and accurately control the desired cell temperature when the disposable cartridge is inserted into the portable diagnostic device. The temperature sensing probe is preferably one of a type of scanning infrared thermocouple probes which combine speed and accuracy with a readily usable output signal.

BRIEF DESCRIPTION OF THE DRAWINGS

In the drawings, wherein like numerals are utilized to designate like parts throughout the same:

FIG. 1B is an exploded view of the perspective instrument sub-assembly of FIG. 1A;

DETAILED DESCRIPTION

The instrument sub-assembly depicted in the several views of the drawings is part of a larger portable instrument which makes analytical determinations such as blood gas analysis. The instrument uses a disposable cartridge which contains a calibrated electrochemical cell designed to receive and electrochemically measure a sample injected into a sample port associated with the cartridge. The integral electrochemical cell of the cartridge is carried on a sensor chip and includes a resistive heating element also preferably formed on the sensor chip member. Electric input to the heating element is thermostatically controlled by a non-contact temperature sensitive device, such as a scanning infrared probe, which monitors the temperature of the outer surface of the sensor chip and controls input to the resistive heating element through conventional temperature control circuitry. Of course, the particular embodiment shown is merely illustrative of the several unique features and principles which may be more broadly applied by those skilled in the art.

Figure 1A:
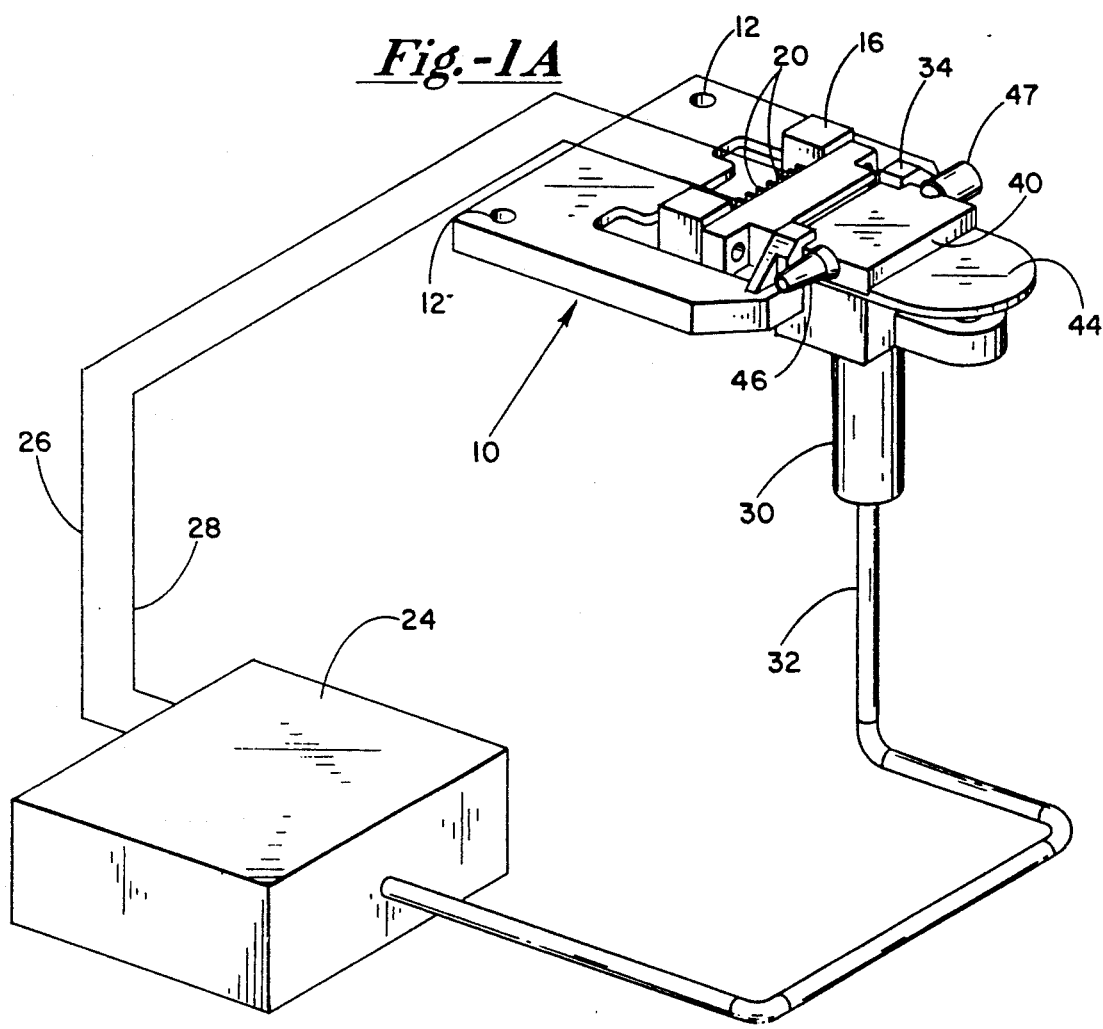
FIG. 1A is a fragmentary perspective instrument sub-assembly view depicting the sample measurement cartridge temperature control system of the invention.

Accordingly, FIGS. 1A and 1B depict, in perspective, and partially schematically, an instrument sub-assembly integral with a larger device and including a removable cartridge and cartridge receiving retaining device together with a temperature control system for the removable cartridge. The system includes an instrument sub-assembly housing shown generally at 10 which may be fastened to the main body of a larger portable instrument (not shown) as by utilizing openings or holes 12 in the housing. As can best be seen by FIG. 1B, the housing 10 further contains a recess 14 and a connecting block 16 for receiving and retaining, as by screws (not shown), an electrical connector or terminal block 18. The connector 18 includes a plurality of electrical input/output terminals 20 which physically retain and electrically connect a removable cartridge system, depicted generally at 22, with the main portion of the analytical instrument (not shown) as required.

The connector element 18 is shown schematically connected to conventional temperature control circuitry which operates in a well-known manner and is designated by the box 24 using a pair of conductors 26 and 28. The temperature sensing input for the temperature control system is provided by a non-contact temperature sensor which is preferably in the form of an infrared scanning thermocouple device or probe 30 which senses temperature rapidly and accurately. The probe 30 is connected to the temperature control circuitry as by conduit 32. The signal received from the probe is processed by the temperature control circuitry and compared with a value corresponding to a fixed designed set point control temperature determined by the application involved, typically about 37° C. or body temperature.

Figure 2:
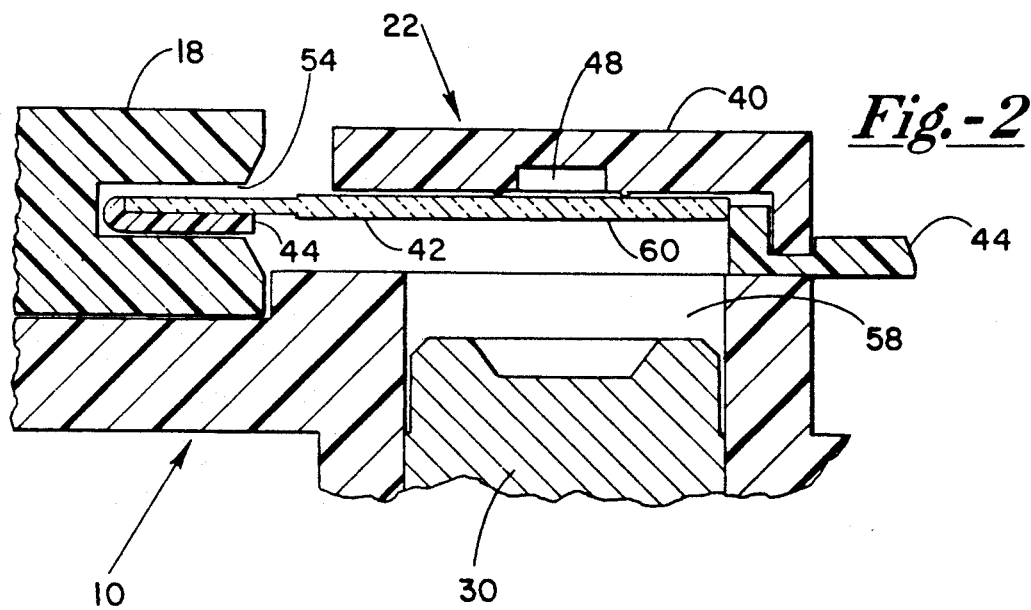
FIG. 2 is an enlarged, fragmentary sectional view of a portion of the system of FIGS. 1A and 1B.
Figure 3:
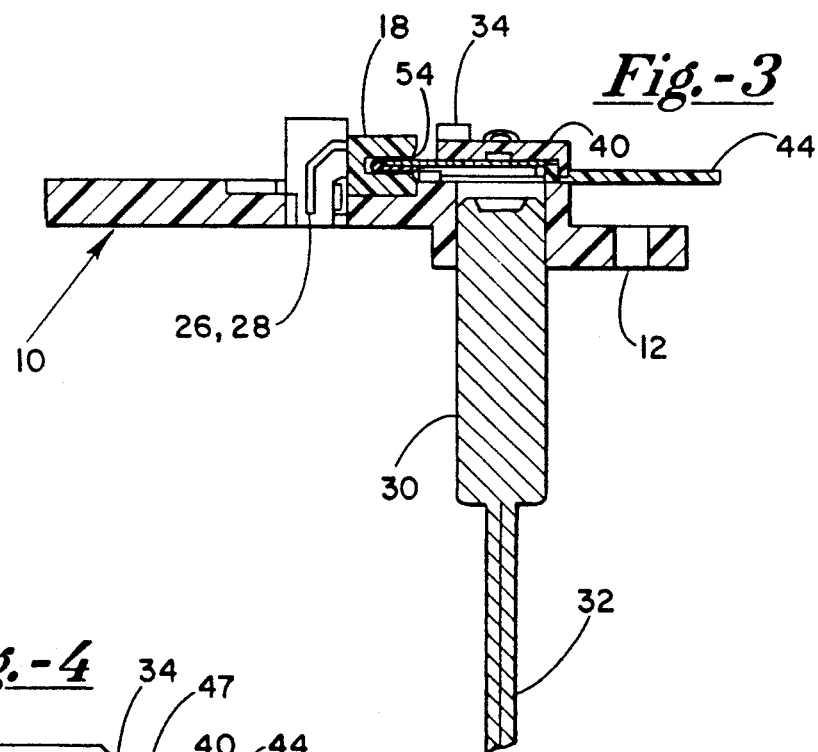
FIG. 3 is a sectional view taken substantially along line 3-3 of FIG. 4.
Figure 4:
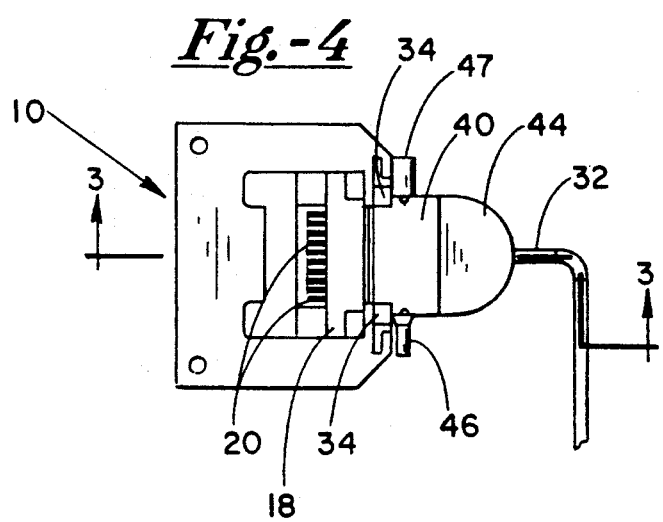
FIG. 4 is a top view of the system of FIGS. 1A and 1B.

The housing 10 contains a pair of integral retainers 34 which are configured to fit over and slidably receive the removable sample cartridge system 22. The sample cartridge, of course, is depicted in the exploded view of FIG. 1B, and includes a top member 40, sensor chip 42 and a base member 44. The top member 40 further includes port 46 which is used to admit a temperature probe for experimental verification purposes. A sample, receiving port is located at 47. As illustrated in FIGS. 2-4, the top member 40 contains a recess which, with the sensor chip member 42, forms a volume 48 for containing the sample. The chip 42 further contains a plurality of electrodes illustrated by 50 and carries a serpentine resistance heating element 52 which is electrically connected to the conductors 26 and 28 utilizing the connector 18 when the cartridge 22 is plugged into the recess 54. The lower member or base member 44 is recessed to receive the chip 42 and further contains a central opening 56 which provides an external window to expose the outer surface 60 of the chip 42. The opening 56 aligns with an opening 58 provided through the housing member 10 giving the probe 30 a direct line of sight of the outer surface 60 of the chip member 42 for the purpose of temperature detection.

The probe 30 may be any suitable scanning infrared sensor, or the like. Examples include one known as IR t/c ® available from Exergen Corporation of Newton, Mass. Such probes can be produced and pre-calibrated in quantity prior to manufacture of the portable measuring instruments so that they will repeatably, rapidly and accurately control the temperature of the observed surface, for example, at 37° C. ±0.2° C. The signal produced by the temperature sensed by the probe 30 is transmitted by a conduit 32 to the control circuitry 24 which, in turn, controls the electric power in conductors 26 and 28 to modulate the energy output of the serpentine resistance element 52 in a well-known manner.

In operation, a fresh disposable cartridge is inserted into the portable instrument so that proper electrical connection is made in opening 54 and the cartridge is also retained in place by ears 34. In connection with this operation, the temperature control system can be automatically activated by the insertion of the cartridge into the receptacle 54. The system may contain any desired time delay circuits or other activation system. Of course, the device may also be controlled by other means such as an instrument switch (not shown) in a well-known manner.

Figure 5:
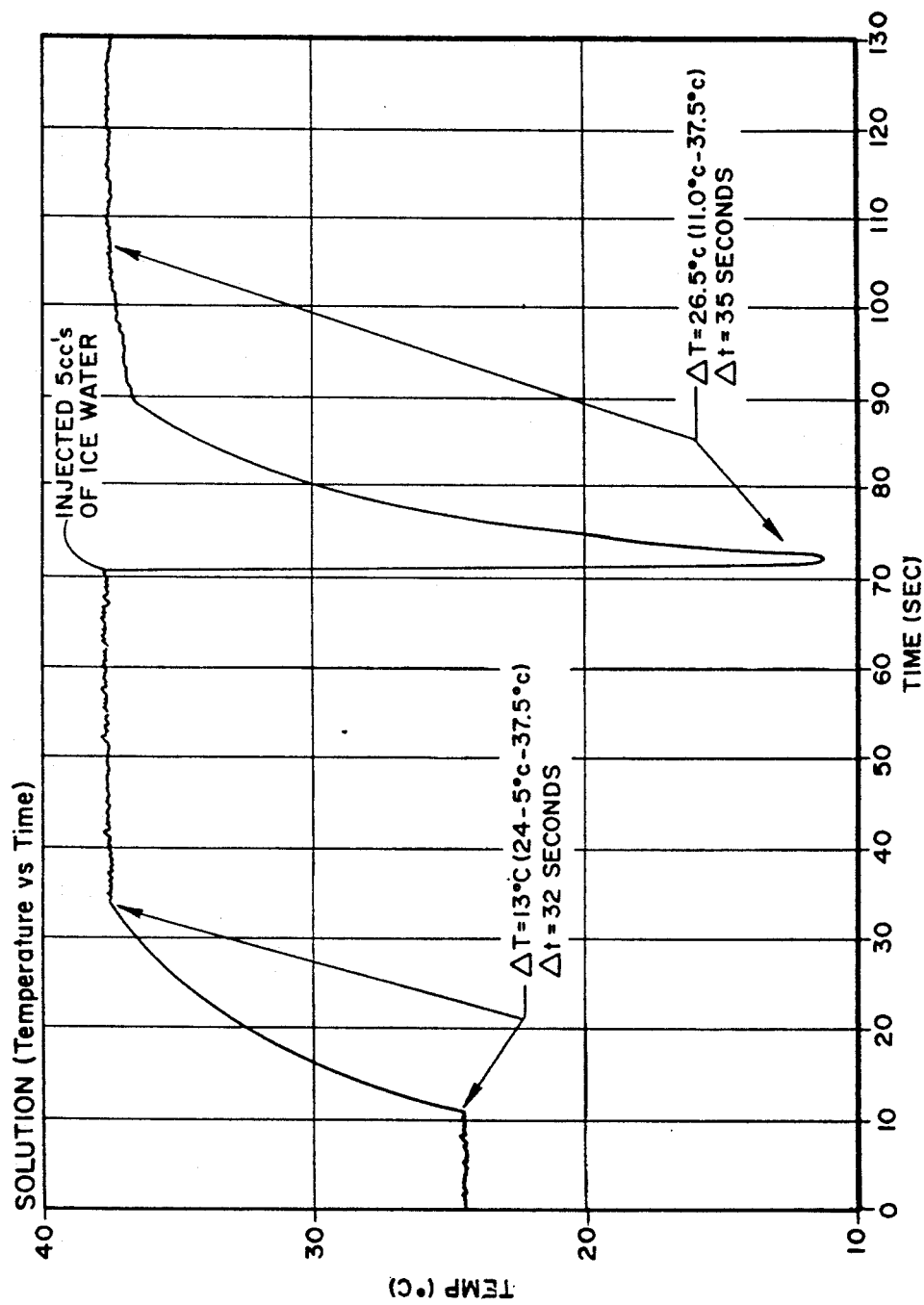
FIG. 5 is a computer generated plot depicting the temperature control of the sample solution in the electrochemical cell of a cartridge in accordance with the invention including reaction to induced traumatic temperature stimuli.

FIG. 5 depicts a computer generated graphical plot illustrating the ability of the temperature control system of the invention to control the solution temperature of the electrochemical cell volume 48 of a disposable cartridge made in accordance with the preferred embodiment. The probe and temperature control circuitry are designed to control the temperature of the solution in the electrochemical cell at about 37.5° C. when stabilized. The time-temperature plot of FIG. 5 illustrates the reaction of the system after activation at approximately 10 seconds into the time plot along the abscissa. The temperature data for the plot of FIG. 5 was obtained by means of a temperature probe inserted into the cell through port 46. Actual temperature values sensed by the probe may be mathematically compensated in the control circuitry to represent actual sample solution temperatures in the cell. The time-temperature profile using the inserted temperature probe in any event is quite similar and representative of the control capabilities of the system. As can be seen from FIG. 5, the temperature was raised from an ambient temperature of approximately 24° C. to the control temperature of approximately 37.5° C. at the 32-second mark. At approximately the 71-second mark, the system was shocked by the injection of approximately 5 cc of ice water as through the port 47. Within about 1-2 seconds, the temperature dropped to approximately 11° C., the low point of the cycle. Thereafter, the recovery was again extremely rapid and reached the control point of approximately 37.5° C. in about 35 seconds. FIG. 5 aptly illustrates the rapidity with which the system recovers to the desired control temperature and the accuracy with which that temperature can be maintained in accordance with the invention.

The chip member 42 is normally fabricated of a thin ceramic with a fairly low thermal capacity for easy temperature control and quick recovery. The serpentine resistive heating element together with connecting conductors is normally deposited on the surface of the chip using screen printing thick film or one of many well-known metallizing techniques. Such resistive heaters may be made of any conventional material such as permalloy (an alloy having a preferred composition of 80% nickel and 20% iron). The material may be deposited as a thick or thin film in any desired configuration. The chip 42 itself may be any ceramic or other convenient dielectric material which meets the criteria for both the electrochemical cell and lends itself to temperature control utilizing the heating system of the invention.

This invention has been described herein in considerable detail in order to comply with the Patent Statutes and to provide those skilled in the art with the information needed to apply the novel principles and to construct and use embodiments of the example as required. However, it is to be understood that the invention can be carried out by specifically different devices and that various modifications can be accomplished without departing from the scope of the invention itself.

For example, the resistive heating element 52 can be replaced by a different heating means such as a remote millimeter wave generating device or other radiant heating device. Of course, the invention also contemplates use with devices which require temperature control but which do not require an electrochemical cell.

We claim:

1. A temperature control system for controlling the temperature in a disposable cartridge sampling unit for a portable diagnostic system comprising:
   a disposable cartridge further comprising;
      means for containing a sample volume,
      a sensor substrate having oppositely disposed inner and outer surfaces, the inner surface being in contact with the sample volume and carrying one or more electrochemical cell means for making one or more measurements with respect to a sample placed therein, the sensor substrate further carrying integral electrical heater means,
      electrical conductor means for conducting electrical energy to the heater means;
   mounting means for removably receiving and electrically connecting the disposable cartridge to a larger, portable diagnostic device;
   temperature sensing means for sensing the temperature of a surface of the sensor substrate without direct contact with the cartridge or direct exposure to the heating element itself and generating an electrical signal related to the sensed temperature;
   control means for controlling the electrical input to the heater means based on the sensed temperature and a designed control temperature.

2. The apparatus of claim 1 wherein the temperature sensing means is an infrared probe.

3. The apparatus of claim 1 wherein the electrical heater means is a resistance heater integral with one surface of the sensor substrate.

4. The apparatus of claim 3 wherein the electrical heater means is a thick film resistor and the sensor substrate is a dielectric chip.

5. The apparatus of claim 4 wherein the surface of which the temperature is sensed is the sensor substrate surface opposite that carrying the thick film resistor.

6. The apparatus of claim 5 wherein the temperature sensing means is an infrared probe.

7. The apparatus of claim 5 wherein the temperature control system includes means activating the temperature control system which is activated by connecting the disposable cartridge in the mounting means.

8. The apparatus of claim 4 wherein the temperature sensing means is an infrared probe.

9. The apparatus of claim 1 wherein the surface of which the temperature is sensed is the sensor substrate surface opposite that carrying the electrochemical cell means.

10. The apparatus of claim 9 wherein the temperature sensing means is an infrared probe.

11. The apparatus of claim 1 wherein the temperature control system includes means activating the temperature control system which is activated by connecting the disposable cartridge in the mounting means.

* * * * *